United States Patent [19]

Wiseman et al.

[11] 3,934,965

[45] Jan. 27, 1976

[54] OPTICAL COUPLER

[75] Inventors: Donald F. Wiseman, Hackensack; Roy C. Josephsen, Hillsdale, both of N.J.

[73] Assignee: Technicon Instruments Corporation, Tarrytown, N.Y.

[22] Filed: Oct. 29, 1974

[21] Appl. No.: 518,677

[52] U.S. Cl. ................ 356/246; 250/227; 250/576; 356/244
[51] Int. Cl.² .......................................... G01N 1/10
[58] Field of Search .............. 23/259; 356/246, 244; 250/576, 277; 350/96

[56] References Cited
UNITED STATES PATENTS

| | | | |
|---|---|---|---|
| 3,459,304 | 8/1969 | Brenchley | 250/576 |
| 3,513,319 | 5/1970 | Broerman | 250/227 |
| 3,740,158 | 6/1973 | Bellinger et al. | 350/96 R |
| 3,819,278 | 6/1974 | Muller | 356/246 |

*Primary Examiner*—James W. Lawrence
*Assistant Examiner*—D. C. Nelms
*Attorney, Agent, or Firm*—S. P. Tedesco, Esq.; S. E. Rockwell, Esq.

[57] ABSTRACT

A quick-disconnect coupler for a light-transmitting flowcell having in a sight path light-input and light-output windows, respectively, for interposition intermediate a light source and a light detector, respectively, at least in part through a pair of elongated light-transmitting elements, and a support member for the flowcell. There is provided a slip-on flowcell supported on the support member, and a quick-release clamp comprising a pair of jaw members having a pair of corresponding end portions and comprising mounting means for movement of said end portions respectively toward and away from each other and said flowcell windows. The light-transmitting elements have terminals supported in the respective jaw members for alignment with the respective flowcell windows and in contact with said flowcell in the operative positions of the jaws. Further, there is in the combination slip-on coacting guide means on the support member and the clamp to support the clamp in an operative position with respect to the flowcell.

12 Claims, 5 Drawing Figures

FIG. 1
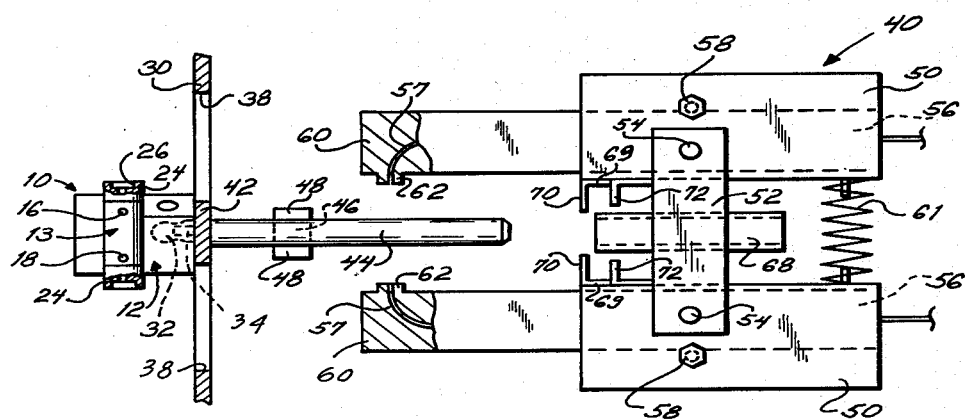
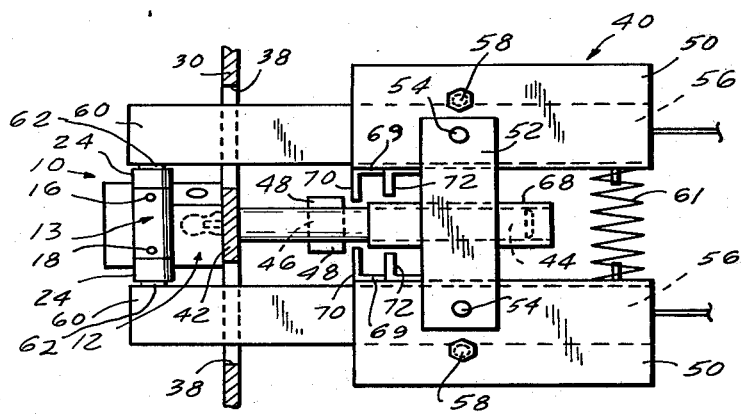
FIG. 2

OPTICAL COUPLER

BACKGROUND OF THE INVENTION

1. Field of the Invention

The present invention relates to a quick-disconnect optical coupler or coupling in the light path of a flowcell.

2. Prior Art

Heretofore an optical coupling in a sight path through a flowcell has been attempted, which sight path is formed at least in part through a pair of elongated transmitting elements, such as optical fibers, interposed intermediate the respective flowcell windows and a light source and light detector, respectively. Such a coupling has included a fixed support for the flowcell and a clamp means comprising a pair of jaw members, the light-transmitting elements having terminals supported in the respective jaw members for alignment with the respective flowcell windows in the operative positions of the jaws. The construction was awkward, clumsy, and the jaws were difficult to align with the flowcell windows. Upon such alignment a user was required to clamp the jaw members together as by a resilient C clamp. There was no quick-disconnect of the flowcell from its support. Furthermore, the jaw members could not be quickly removed from the flowcell for complete clearance of the jaw members with the flowcell, while the jaw members were maintained in such clearance positions. The clamp was aligned in a horizontal plane by a bolt located in a threaded hole of the support to provide both alignment of the clamp in a plane normal to the sight path through the flowcell and in a plane parallel thereto. The jaws each had flanges through which the bolt passed with clearance, and nuts were provided on the bolt to coact with the flanges and hold the clamp jaws in the desired position in a plane normal to the flowcell sight path. To remove the optical coupling completely from the support, it was necessary to remove the aforementioned nuts, to remove the jaw members from the bolt, which provided a pivot for the jaw members, and to remove the bolt from the support. This was tedious and time consuming and, as previously indicated, it was also tedious and time consuming to assemble the optical coupling on the support.

The present invention involves obviating all of these problems.

SUMMARY OF INVENTION

One object of the invention is to provide an improved optical coupling for or a coupler including a flowcell. A further object is to provide in such coupling a quick-disconnect feature. Still another object is to provide means by which either or both the optical coupling and the flowcell may be quickly and easily aligned. Another object is to provide means by which either or both the flowcell and the optical coupling may be quickly and easily supported and disassembled from such support. Further objects of the invention will appear from the detailed description of a presently preferred embodiment of the invention. There is provided in an optical coupling for a light-transmitting light cell having in a sight-path light-input and light-output windows, respectively, for interposition intermediate a light source and a light detector, respectively, at least in part through a pair of elongated light-transmitting elements and a fixed support for the flowcell, the improvement of: an optical clamp comprising a pair of jaw members having a pair of corresponding end portions and comprising mounting means for moving such end portions relatively toward and away from each other and such flowcell windows, the light transmitting elements having terminals supporting in the respective jaw members for alignment with respective windows in the operative position of said jaws, and slip-on coacting guide means on such clamp and such support for aligning such clamp in planes normal and parallel to such sight path.

BRIEF DESCRIPTION OF THE DRAWINGS

In the drawings:

FIG. 1 is a fragmentary view partially broken away in top plan illustrating an optical coupling just prior to assembly of the latter with a flowcell on a support, and embodying the invention;

FIG. 2 is a view similar to FIG. 1 showing the coupling in assembled condition;

FIG. 4 is a view similar to FIG. 2 but illustrating the optical coupling in condition in which the jaws are maintained in open and released condition when the flowcell is removed from the support; and.

DETAILED DESCRIPTION OF THE PREFERRED EMBODIMENT OF THE INVENTION

Figure 3:
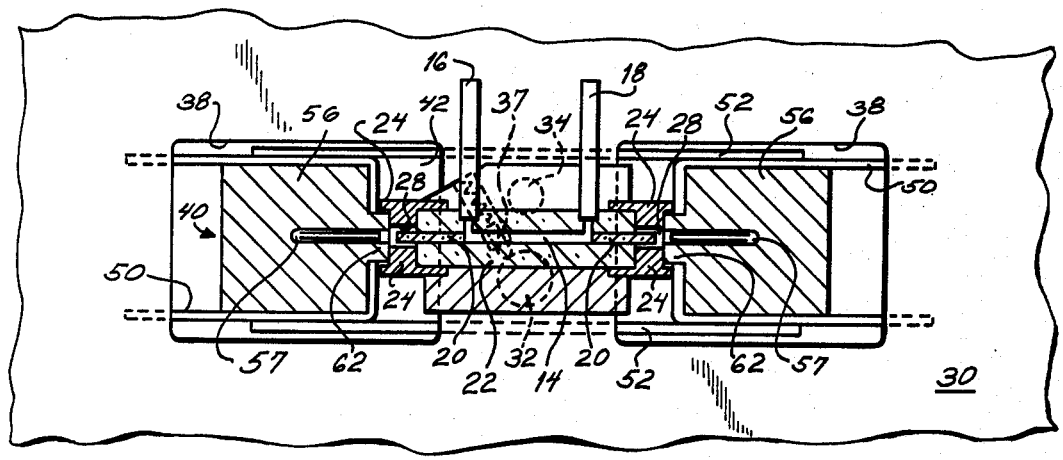
FIG. 3 is an enlarged, sectional view taken on line 3—3 of FIG. 2.

As best seen in FIGS. 1 and 3 there is shown a flowcell indicated generally at 10. The flowcell comprises a holder portion 12 conventionally supporting an elongated flowcell body element 13 constructed in accordance with Bellinger, et al, U.S. Pat. No. 3,740,158 having flow path 14, inlet and outlet nipples 16 and 18 respectively, and rod-like end windows 20, structured of a material having higher refractive index than the body 13 of the flowcell in which the flow path extends and forming a light pipe. A pair of metal caps 24, are attached to the respective ends of the elongated body 22, the caps 24 each having an outwardly facing socket 26 therein. The caps do not touch the rods 20, and in the central region of each cap, in alignment with the corresponding rod 20, there is an aperture 28.

The flowcell is supported from a base 30, which may have the form of a manifold plate, such as the plate 16 of the manifold described in Diebler, et al., U.S. Pat. No. 3,811,842. The manifold shown in that patent may be one of the multiplicity of chemical test cartridges 80 described in Smythe, et al., U.S. Pat. No. 3,826,615. The support for the flowcell 10 may comprise pins 32, 34, which are of different diameter and extend into complemental sockets formed in the holder part 12 of the flowcell 10. A spring-pressed ball detent 37 supported in the holder coacts with the pin 32 so that the flowcell snaps on and off the base 30 for removal of the flowcell for cleaning or for replacement thereof. This pin and socket construction and arrangement prevents incorrect assembly of the flowcell 10 with the base 30. While the flowcell may have the rod-like end windows 20 of the aforementioned Bellinger et al. Patent, the flowcell end windows may take the form of those shown in Rosin et al., U.S. Pat. No. 3,345,910 which are planar and flush with the ends of the flowcell body, or the curvilinear end windows for better flow characteristics through the cell, shown in FIG. 7 of Skeggs, et al., U.S. Pat. No. 3,241,432.

The base or manifold plate 30 has clearance openings 38 therein for portions of the optical coupling comprising a clamp indicated generally at 40. The flowcell 10 is supported on a portion 42 of the plate 30 intermediate the cutaway portions 38. The pin 32, extending through the plate portion 42 supporting the flowcell, may have a reduced portion which may be threaded in a non-illustrated, conventional manner into the front end of a guide post 44 at the opposite face of the plate 30 to support the post from the plate. The pin 34 may be formed integrally on the front end of the post 44 to extend through the plate portion 42 and into the corresponding flowcell socket, and the guide post 44 coacts with the optical clamp 40. The guide post 44 is out-of-round, and is of rectangular cross-section in the form illustrated by way of example. Intermediate the ends thereof, an abutment is in fixed relation to the guide post 44 and, as illustrated, takes the form of a pin 46 extending through guide post 44 transversely thereof and having protruding ends 48.

In the illustrated form, the optical clamp 40 comprises a pair of channel members 50 spaced from one another with the bottoms of the channel members in opposing relation to one another. A pair of straps 52 interconnect the channel members 50 by two pairs of pivots fixed in the respective channel members 50, the pivots of one pair being indicated at 54. Two arms 56 of a cross section complemental to the cross sectional shape of the channel members 50 are provided. Each arm 56 bottoms in the corresponding one of the channel members 50 and is secured there against by one of a pair of bolts 58 extending through the channel members 50. The arms 56 provide at their forward end portions a pair of jaws indicated at 60. Each arm 56, may, on the side thereof nearest the other arm, be grooved longitudinally substantially throughout the length of the arm to receive one of a pair of optical fibers 57 in the bottom thereof which extends through the rear end of the arm 56 and at its forward end portion is bent on a radius to provide at the near extremity thereof a terminal. Such non-illustrated groove may then be filled with a cementitious substance. Such terminals, in the condition of the clamp 40 shown in FIGS. 2 and 3, are in alignment with one another and in alignment with the end windows or rods 20 of the flowcell 10.

While it will be obvious to those versed in the art that the jaws need not be pivotally interconnected, nor interconnected at all, for movement toward and away from one another, in the illustrated form the jaws are pivoted in the manner previously indicated, and a compression spring 61 is interposed between the rear end portions of the channel members 56, urging the jaws 60 toward one another. A pair of male coupling elements 62 are provided. The male coupling elements 62 are provided on the respective jaws 60 and are preferably cylindrical, the female sockets 26 of the caps 24 the flowcell 10 being of a complemental cross section. Each of the last mentioned terminals of the respective optical fibers 57 terminates short of the outer extremity of the male coupling element 62 and the male coupling 62 has a central opening there through which the corresponding fiber optical terminal is exposed. In the coupled condition of the optical clamp 40 and flowcell 10 of FIGS. 2 and 3, the spacing between each optical fiber and the corresponding flowcell end window 20 is preferably in the range of 0.001 – 0.008 inch. In the condition of the optical clamp 40 of FIG. 2 the optical elements are in accurate alignment and dislocation of the jaws with respect to the flowcell is prevented by the aforementioned male and female coupling elements. Further, as indicated by FIGS. 1 and 2, when the optical clamp 40 is being assembled, from the position and condition of FIG. 1 to the assembled condition of FIG. 2, the jaws 60 are moved forwardly through the clearance openings 38 in the base plate 30. To maintain the optical clamp 40 in the position of FIG. 1 wherein the spring-biased jaws are in substantially parallel position, manual pressure is exerted on channel members 50, compressing the spring 61. In the condition of the coupling in FIG. 2 such manual pressure is released.

The straps 52 support therebetween in a conventional fixed manner as by welding a forwardly extending straight sleeve 68 of a cross section complemental to the cross section of the guide post 44 for cooperation therewith and to slip over the latter. It will be noted that the guide post 44 coacting with the sleeve 68, locates the optical clamp in planes parallel and normal to the plane of the flow or sight path 14 of the flowcell 10, and also locates the optical clamp 40 angularly with respect thereto, the sleeve 68 like the post 44 being of rectangular cross section in the illustrated form. If desired, there may be a friction fit or spring coacting between the guide post 44 and the sleeve 68 to further prevent dislocation of the coupling between the flowcell and the optical clamp in the condition of FIG. 2, which spring is not illustrated and which is not believed to be necessary.

Figure 4:
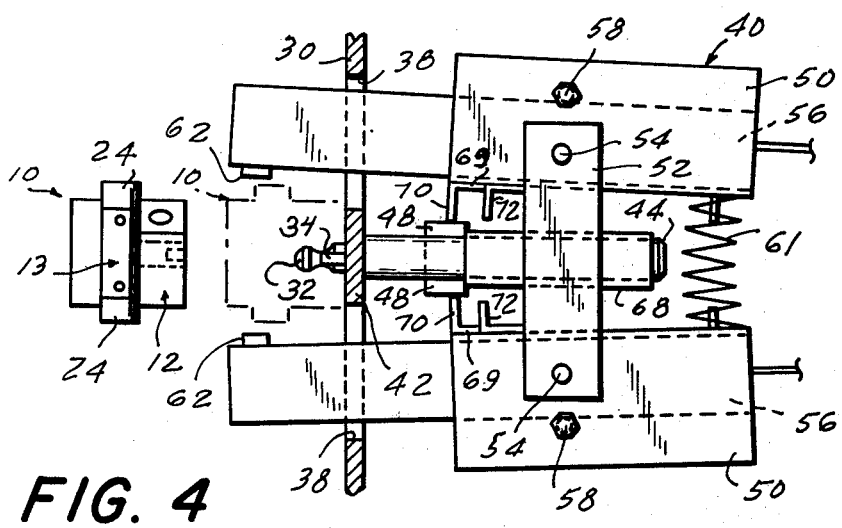

To release the clamp 40 from the flowcell and park it, and permit the flowcell to be removed from the base plate 30 in the condition of FIG. 4, the rear ends of the clamp 40 are compressed and the clamp 40 is moved forwardly to the position shown in the last mentioned view. A pair of straps 69 are secured as by welding to the under side of the respective channel members 50 and each has a forward right angular flange or stop 70 the outer extremity of which, in the condition of the optical clamp 40 of FIG. 4, abuts the corresponding end surface of the abutment 46 on the post 44 to maintain the clamp 40 in the position shown. In releasing the flowcell from the clamp 40 as aforesaid, the rear end of the channel members 40 may be manipulated to compress the spring 61 sufficiently to allow the stops 70 to initially clear the abutment pin 46, while moving the clamp 40 forwardly until the forward end of the sleeve 68 abuts the abutment 46 in the manner shown in FIG. 4, wherein the clamp 40 is essentially latched to the guide post 44. When the flowcell 10 is subsequently removed and replaced and snapped on to pin 32 in the aforementioned manner, the rear ends of the channel member 50 may be compressed sufficiently to allow the stops 70 to clear the ends of the abutment pin 46, after which the optical clamp 40 may be readily moved rearwardly to the extent necessary to align the male and female coupling elements of the flowcell and the jaws 60.

Figure 5:
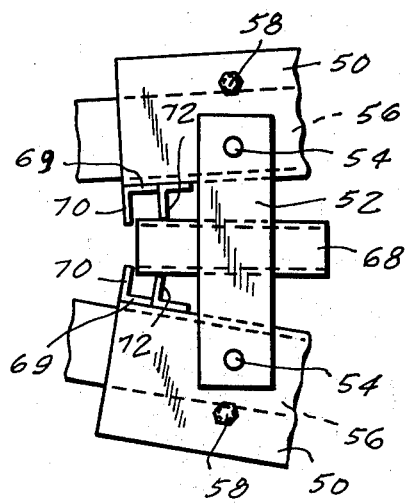
FIG. 5 is an enlarged, fragmentary, top plan view illustrating the clamp in a condition in which it is disassembled from the support.

In FIG. 5 the optical clamp 40 is in a condition in which it is entirely disassociated from the base plate 30 and the guide post 44. The aforementioned pair of straps 69 each has, in laterally offset relation to the stop 70, a similar flange or stop 72, which in the last mentioned condition of the clamp 40 abuts the sleeve 68 to limit the extent of closing movement of the jaws 60 under the influence of the spring 61. This enables non-illustrated cover elements to be slipped over the respective jaws to protect the optical terminals thereon and the male coupling members 64 from being damaged. These cover elements may be formed of a hard plastic material.

While only one embodiment of the invention has been illustrated in the drawing and described above, it will be apparent, especially to those versed in the art, that the coupling or coupler may take other forms and is susceptible of various changes in detail, without departing from the principles of the invention.

What is claimed is:

1. In an optical coupling for a flowcell having an optical sight path and light-input and light-output windows along said sight path the combination of: a support for the flowcell, clamp means comprising a pair of jaw members having a pair of corresponding end portions and comprising means for movement of such end portions relatively toward and away from each other, at least a pair of light-transmitting elements having terminals supported in the respective jaw members for alignment with said light-input and light-output windows, respectively, in the operative positions of said jaws, and slip-on coacting guide means on said clamp means and said support for aligning said light-transmitting elements along said optical sight path in the operative positions of said jaws.

2. An optical coupling as defined in claim 1, wherein: said coacting guide means on said clamp means and said support comprises support means for angular alignment of said clamp means.

3. An optical coupling as defined in claim 1, wherein: said coacting guide means on said clamp means and said support comprises a post on one element and a sleeve on the other of the elements.

4. An optical coupling as defined in claim 1, wherein: said coacting guide means on said clamp means and said support comprises a post on said support and a sleeve on said clamp means.

5. An optical coupling as defined in claim 1, further including coacting means on said jaw and said flowcell preventing dislocation of said clamp means in a plane normal to said sight path when assembled with the flowcell.

6. An optical coupling as defined in claim 1, further including means biasing said corresponding end portions of the jaw members toward one another, and stop means on said clamp means for limiting movement of said corresponding end portions of the jaw members toward one another when said clamp means is removed from said support.

7. An optical coupling as defined in claim 1, wherein: said coacting guide means comprises an element on said support and an element on said clamp means, one of said elements having means thereon coacting with means on the other of said elements to support said clamp from said other element in an open and flowcell-releasing condition of said jaws.

8. An optical coupling as defined in claim 1, wherein: said coacting guide means comprises an abutment in fixed relationship with said support cooperating with stop means on said clamp to support said clamp from said abutment in an open and flowcell-releasing condition of said jaws.

9. Apparatus as defined in claim 1 wherein said light-transmitting elements are formed of optical fibers and coact with said end windows of said flowcell which are structured with rods respectively.

10. A quick-disconnect coupler as defined in claim 1, wherein: said clamp means is removably supported by said support member when said clamp means is not coupled to said flowcell.

11. An optical coupling as defined in claim 7, wherein: said guide means on said clamp means provides an abutment which in the last-mentioned position of said jaws abuts said fixed abutment to position said clamp means against dislocation along a plane normal to said sight path.

12. In a quick-disconnect coupler for a light-transmitting flowcell having in a sight path light-input and light-output windows, respectively, for interposition intermediate a light source and a light detector, respectively, at least in part through a pair of elongated light-transmitting elements, and a support member for the flowcell, the improvement of: a slip-on flowcell supported on said support member, quick-release clamp means comprising a pair of jaw members having a pair of corresponding end portions and comprising means for movement of said end portions relatively toward and away from each other and said flowcell windows, said light-transmitting elements having terminals supported in the respective jaw members for alignment with the respective flowcell windows and in contact with said flowcell in the operative positions of said jaws, slip-on coacting means on said support member and said clamp means to support the clamp means in an operative position with respect to said flowcell windows.

* * * * *